United States Patent [19]

Martens

[11] Patent Number: 4,559,825

[45] Date of Patent: Dec. 24, 1985

[54] TRANSDUCER ARRAY FOR DETECTION OF SUBSURFACE FLAWS

[75] Inventor: George D. Martens, New Milford, Conn.

[73] Assignee: Automation Industries, Inc., Greenwich, Conn.

[21] Appl. No.: 580,268

[22] Filed: Feb. 15, 1984

[51] Int. Cl.⁴ .............................................. G01N 29/04
[52] U.S. Cl. ........................................ 73/622; 73/623
[58] Field of Search ................. 73/622, 623, 638, 637, 73/641, 639, 588, 628; 376/252

[56] References Cited

U.S. PATENT DOCUMENTS

| | | | |
|---|---|---|---|
| 3,850,028 | 11/1974 | Thompson et al. | 73/638 |
| 4,041,773 | 8/1977 | Hauldren et al. | 73/622 |
| 4,196,607 | 4/1980 | Youtsey et al. | 73/622 |
| 4,289,033 | 9/1981 | Prause et al. | 73/622 |

FOREIGN PATENT DOCUMENTS

| | | | |
|---|---|---|---|
| 1121767 | 7/1968 | United Kingdom | 73/628 |
| 185534 | 10/1966 | U.S.S.R. | 73/628 |

Primary Examiner—Anthony V. Ciarlante
Attorney, Agent, or Firm—Thomas L. Flattery

[57] ABSTRACT

A system of transducers and electrical circuitry connecting with the transducers detects and locates flaws in the metallic walls of vessels used for containing and transporting liquids. An array of transducers is carried by a sled having rollers for facile movement about the surface of the vessel which surface is submerged within the liquid to permit the liquid to provide a sound propagating medium between the transducers and the vessel wall. The transducers are arranged in sets of two transducers, one of which is a transmitting transducer and the other a receiving transducer, the two transducers being positioned in tandem for increased azimuthal coverage of the sonic radiation.

10 Claims, 5 Drawing Figures

TRANSDUCER ARRAY FOR DETECTION OF SUBSURFACE FLAWS

BACKGROUND OF THE INVENTION

This invention relates to the transmission of sound in the walls of vessels, such as those used for containment of liquids in nuclear reactors, for the detection of flaws within the material of the walls and hidden below the surface of a wall. More particularly, the invention relates to the positioning of plural sets of transmitters and receivers in an array for observation of such flaws from different directions.

At many industrial sites, particularly at nuclear reactors, large vessels are constructed for the containment of liquids such as water. The vessels may be formed as tanks for holding the liquid at one location, or in the form of conduits for transporting the liquid from one location to another. These vessels are frequently constructed of a steel wall, sections of which may be welded togethr during the construction process. For example, the base metal of the wall may be a carbon steel which is sufficiently strong for holding the liquid under pressure. In addition, the wall may be clad with a protective skin such as a layer of ¼ inch thick stainless steel. The stainless steel protects the vessel from corrosive substances that may be present within the liquids. In particular, it is noted that great care is required in assembly of the vessels to minimize all chances of failure including failures due to stresses of high pressure.

A problem arises in that a flaw may occur in the material of the wall, particularly at the site of a weld. Such flaw may be hidden from view by the outer cladding of the stainless steel skin. One attempt at the detection and location of such flaws has employed the use of a sonic transmitter and receiver which are mounted in a side-by-side arrangement for direction of sonic energy towards the flaw, and for reception of sonic energy reflected back from the flaw. With the foregoing arrangement, the flaw lies on a plane located between the transmitting and receiving transducers. As a result, the rays of energy tend to focus primarily upon the flaw and reduce the possibility of detection of sonic echoes at a location other than at the flaw. The two transducers must be scanned together in different directions about the surface of the vessel wall to ensure detection of a flaw. Such a procedure may be excessively time consuming and also may introduce a risk that the scanning misses a possible flaw.

SUMMARY OF THE INVENTION

The aforementioned problem is overcome and other advantages are provided by a detector arrangement incorporating the invention wherein the transmitting and receiving transducers are arranged in tandem, the two transducers being positioned with their centerlines along a common plane which intersects the flaw. The receiving transducer is positioned behind the transmitting transducer. The two transducers are inclined relative to a wall of a vessel being inspected so that the beams of energy impinge upon the wall surface at an oblique angle. The beams then travel along paths within the wall material which are inclined only slightly with the surface of the wall. This arrangement of the two transducers is advantageous in that the flaw can be detected over a wider range of azimuthal angle.

Four sets of transducers, each having the transmitting and the receiving transducers, can be arranged facing each other in a square array in the general vicinity of the flaw. This arrangement, with the increased azimuth angle associated with each transducer set, provides the beneficial result that there are substantially no blind spots in the detection of the flaw. Thus, by either simultaneous operation of the specific sets of transducers, or by sequential operation of the sets of transducers, the coverage of a region of inspection is attained with a greater probability of success in the detection of flaws.

An additional feature of the invention is provided by mounting the four sets of transducers on a sled which is supported along the surface of the vessel wall by pads which are located at peripheral regions of the sled so as to be out of the paths of sonic radiation of the sets of transducers. The pads position the radiating surfaces of the transducers away from the wal surface so as to avoid direct sonic communication between a transducer and the material of the wall, all such transmission of sonic energy being had through a layer of water within the vessel. In addition, the pads are provided with mechanical rollers to permit the sled to ride along the inner surface of the vessel while the sonic energy is communicated via the water into the wall and back to a transducer. This is advantageous in that there is no frictional contact between a radiating surface and the vessel wall so as to insure that all paths of radiation are free of perturbations which might otherwise be introduced upon wear of the radiating surface by friction.

BRIEF DESCRIPTION OF THE DRAWING

The aforementioned aspects and other features of the invenion are explained in the following description taken in connection with the accompanying drawing wherein.

DETAILED DESCRIPTION

Figure 1:
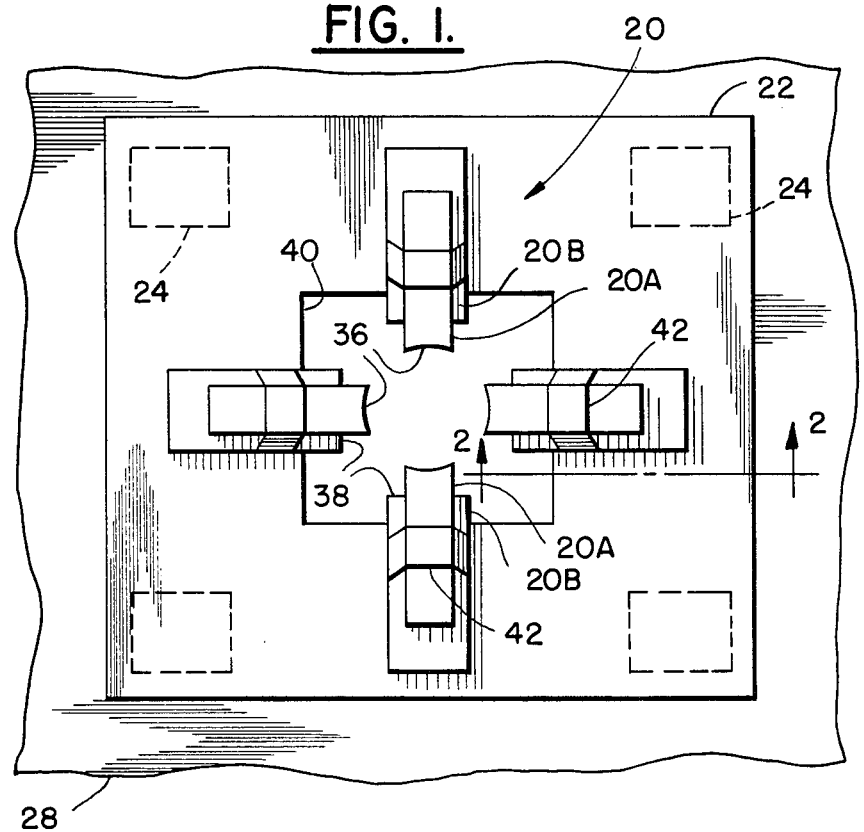
FIG. 1 is a plan view of an array of four sets of transducers carried by a sled on a vessel wall in accordance with the invention.
Figure 2:
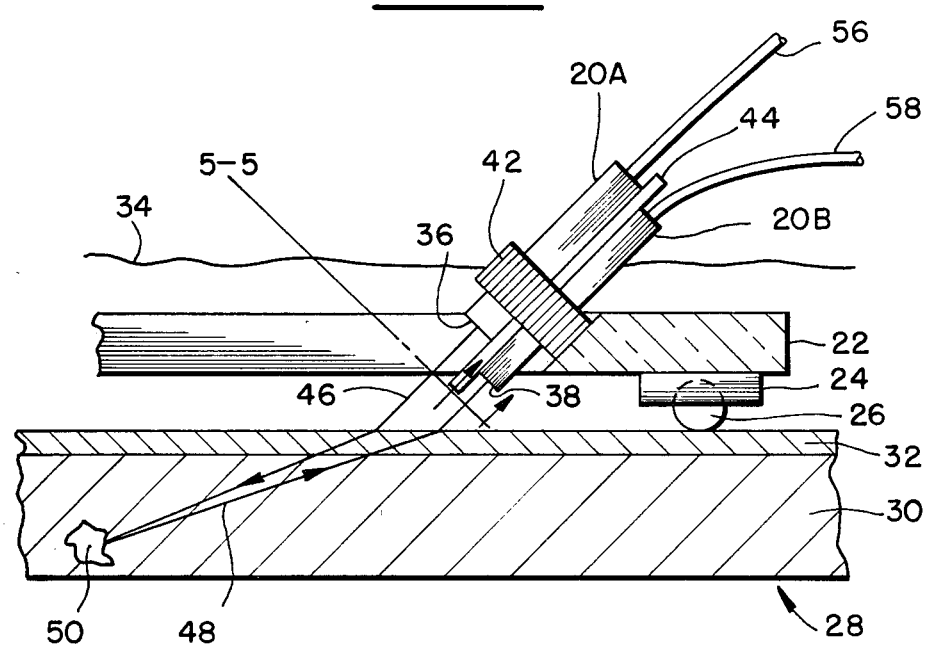
FIG. 2 is a stylized side elevation view of one set of transducers taken along line 2—2 in FIG. 1.

With reference to FIGS. 1 and 2, there is shown an array of transducers 20 which, in accordance with the invention, comprises transmitting transducers 20A and receiving transducers 20B arranged in four sets of transducers of which each set comprises one transmitting transducer 20A and one receiving transducer 20B. The array of transducers 20 is carried upon a sled 22 supported by pads 24 disposed along the peripheral region of the sled 22. The pads 24 are provided with rollers 26 upon which the sled 22 is transported about the surface of a vessel wall 28. The wall 28 comprises a base-metal portion 30 of a rigid material such as carbon steel and is protected with a cladding 32 typically of ¼ inch stainless steel. While the vessel itself has been deleted in the drawing for clarity, it is understood that the interior portion thereof contains a liquid such as water 34, indicated diagrammatically in FIG. 2, through which sound waves can propagate.

In accordance with the invention, the four sets of transducers 20 are arranged about the sides of a square array with the radiating surfaces 36 and 38, respectively, of the transmitting and receiving transducers facing the interior of the square array. The interior portion of the sled 22 has an opening 40 into which the transducers 20 protrude for directing beams of sonic energy to and from the wall 28. The transducers 20A and 20B in each set are secured by a clamp 42 to a side member of the sled 22. In each set, the transmitting and receiving transducers 20A and 20B are separated by a barrier 44 of a sound absorbing material such as a cork or other suitable sheet of sound absorbing material. The barrier 44 provides sufficient isolation between the transmitted sonic energy of the transmitting transducer 20A and the received sonic energy of the receiving transducer 20B so as to insure that a transmission from a transducer 20A does not interfere with reception by a transducer 20B.

As may be seen in FIG. 2, the longitudinal axis of each of the transducers 20 is oriented at approximately 60 degrees relative to a normal to the surface of the wall 28. In any one set of transducers 20, it is preferable to angle the orientation of the receiving transducer 20B relative to the transmitting transducer 20A by approximately 3 degrees. Thus, the receiving transducer 20B may be angled at approximately 63 degrees to the normal to the surface of the wall 28.

With the foregoing orientations of the transducers 20A and 20B in each set, the corresponding transmitting beam 46 and receiving beam 48 intercept a flaw 50 in the base-metal portion 30 of the wall 28. As may be seen by the diagrammatic presentation in FIG. 2, the transmitting beam 46 exits the radiating surface 36 at substantially normal incidence thereto and, thereafter, propagates through the water 34. Thereafter, the transmitting beam 46 impinges upon the cladding 32 and enters therein with a further bending away from the normal to the surface of the wall 28. The transmitting beam 46 continues to propagate and passes through the interface between the cladding 32 and the base-metal portion 30 to impinge upon and be reflected by the flaw 50. The reflected energy appears as an echo and travels along the receiving beam 48 in a path angled slightly relative to the path of the transmitting beam, the receiving beam 48 terminating at the radiatng surface 38 of the receiving transducer 20B.

With respect to the form of vessels being inspected by the equipment of the invention, it is noted that such vessels may be in the form of cylinders having diameters in the range of 90 to 100 inches. The transmitting transducer is approximately one inch wide and the receiving transducer is approximately 1.25 inches wide. Thus, with the array of four sets of transducers, and wherein the radiating apertures of the respective transducers are adjacent each other, the central region of the array has a diameter of approximately two inches while the overall dimensions of the sled are approximately eight inches on a side. The sled is so much smaller than the diameter of the vessel that, as a practical matter, the vessel wall can be regarded as flat as the sled moves about along the vessel wall. With respect to the transmission of the sonic energy, the waves of the sonic energy are longitudinal waves which have a velocity in water which is approximately ¼ the velocity in the steel wall of the vessel. This difference in the speed of propagation results in the well-known bending of the sound beam at the interface between water and the vessel wall as depicted in FIG. 2.

Figure 5:
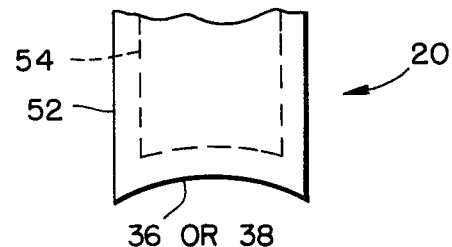
FIG. 5 shows diagrammatically a curvature of the radiating surface of a transducer as viewed along the line 5—5 in FIG. 2.

As shown in the partial view of FIG. 5, each of the transducers 20 is formed with an outer casing 52 of a rigid accoustically dense material such as polyethylene, the casing 52 enclosing a peizoelectric element 54. The element 54 is constructed in accordance with well-known practice in the electro-accoustic art wherein the element 54 may be a crystal of quartz or ceramic material which changes dimensions upon the application of an electric field thereto. The electric field is applied between well-known electrodes (not shown in the drawing) which are excited by a voltage applied long leads 56 and 58 (FIG. 2), respectively, to the transmitting and receiving transducers 20A and 20B. The transformation between sonic and electrical energies is reciprocal at the element 54 so that, in the case of the transmitting transducer 20A, the application of the voltage by the leads 56 includes a mechanical vibration in the form of a sound wave. In the receiving transducer 20B, the element 54 converts the received sound waves to an electric voltage which appears on the lead 58. The polyethylene casing 52 serves as an impedance matching structure for insuring efficient transfer of energy between the element 54 and the water 34.

Figure 3:
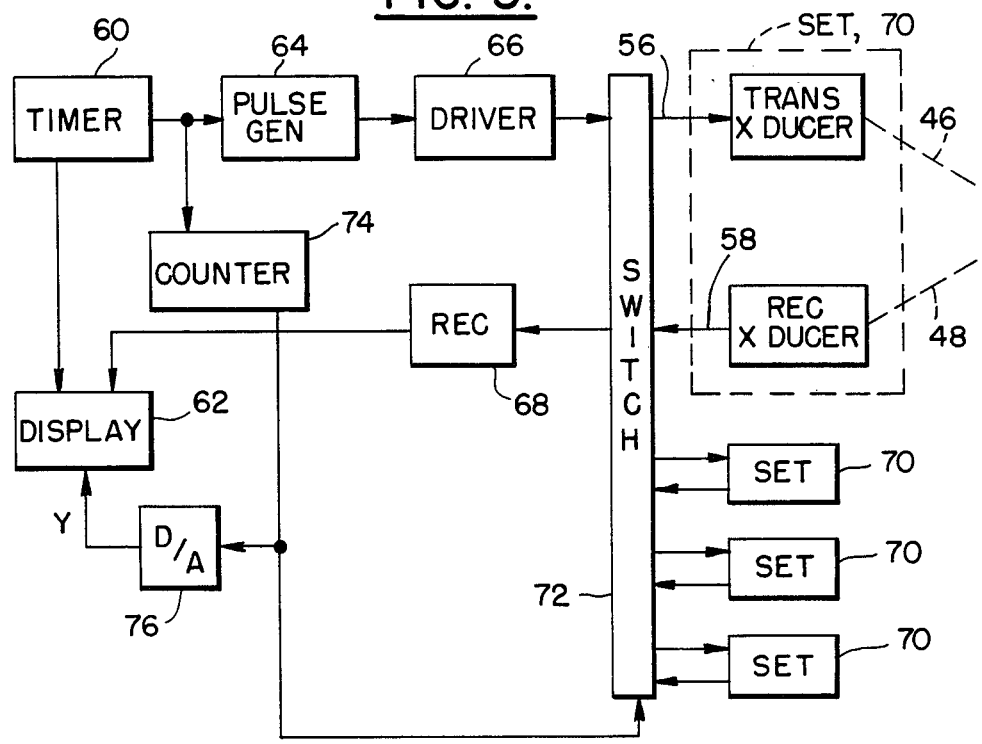
FIG. 3 is an electrical block diagram showing the transmission and reception of signals via a transmitting transducer and a receiving transducer of FIG. 2.
Figure 4:
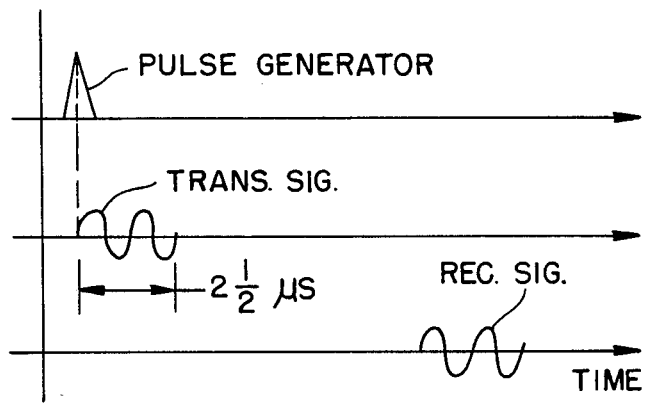
FIG. 4 is a timing diagram useful in explaining signal propagation with the array of the invention.

With reference to FIGS. 3 and 4, conventional electronic circuitry can be employed for energizing the transmitting transducers 20A and for receiving echo signals from the receiving transducers 20B. The circuitry of FIG. 3 comprises a timer 60, a display 62, a pulse generator 64, a driver 66, and a receiver 68 which are interconnected for the transmission and reception of sonic energy via the transducers 20A and 20B. The timer 60 triggers the generator 64 to produce a pulse depicted in the first graph of FIG. 4. The pulse is amplified by the circuitry of the driver 66 to a suitable power level for energizing the transmitting transducer 20A. The duration of the pulse of the generator 64 is less than one microsecond, and introduces an oscillation in the peizoelectric element 54 of the transducer 20A which is sustained for approximately two cycles of a sinusoid at a frequency of approximately 2.25 magahertz, the oscillation being depicted in the second graph of FIG. 4. This signal is then transmitted from the transducer 20A via the water 34 to the vessel wall 28 as has been described with respect to FIG. 2. A typical round-trip propagation time of the sonic signal to the flaw 50 and back to the receiving transducer 20B is approximately eight microseconds. The received signal, apart from some distortion which may be present in the transmission media, is thus a replica of the signal of the second graph of FIG. 4, but delayed by a period of eight microseconds as depicted in the third graph of FIG. 4. The signal is received by the transducer 20B which converts the sonic signal to an electric signal, the electric signal then being amplified by the receiver 68 for presentation on the display 62. The display 62 may be a cathode-ray tube (CRT), and is synchronized to the transmission by a synchronization signal from the timer 60. Thus, the presentation on the display 62 is essentially that shown in the third graph of FIG. 4 wherein the delay in return of the signal is representative of the distance of the flaw 50 from the set of transducers 20A–B employed in the distance measurement.

It is recognized that the foregoing measurement of distance is a radial coordinate of the location of the flaw 50 relative to the set of transducers 20A–B utilized in making the measurement. The precise location of the flaw is not known from the single measurement, this location being determined by further measurements made by further ones of the sets of transducers 20A–B.

To demonstrate the activation of all four sets of transducers 20A–B of FIG. 1, individual ones of the sets 70 are designated in FIG. 3. The circuitry of FIG. 3 further incorporates a selector switch 72 addressed by a counter 74 which, in turn, is pulsed by the output pulses of the timer 60. Thereby, with each pulsation of the timer 60, the counter causes the switch 72 to advance to another one of the sets 70 of transducers 20A–B so as to enable the distance measurement to the flaw 50 to be made from a different angle of view. For example, the successive measurements may proceed clockwise around the sled 22. If desired, a digital-to-analog converter 76 may be coupled between the counter 74 and the y-input terminal of the CRT to provide a succession of four separate horizontal traces on the face of the CRT, with each trace corresponding to one of the transducer sets 70.

In accordance with a further feature of the invention, as is best understood with reference to FIGS. 1 and 5, the radiating surfaces 36 and 38 of the respective transducers 20 may be curved with a predetermined radius of curvature. A slight curvature provides the transducer array with the appearance of a generally square-shaped array with the curvature serving to increase the azimuthal range over which points of reflection such as the flaw 50, can be observed. Alternatively, the curvature of the radiating surfaces 36 and 38 can be increased so as to provide the transducer array with the general form of a circular-shaped array for a still more uniform distribution of the sonic energy in terms of azimuthal angle around the opening 40 in the sled 22. If desired, the signals from two adjacent sets 70 may be combined by well-known circuitry (not shown) to provide the effect of a rotation of the sled 22 by an angle of 45 degrees. Such electronic beam steering is in addition to the mechanical positioning and orienting of the sled 22 along the interior of the vessel.

The foregoing description has presented an array of transducers wherein the transducers are arranged in sets of two transducers. Each set comprises a transmitting transducer and a receiving transducer arranged in tandem, that is, with the radiating aperture of the receiving transducer behind the radiating aperture of the transmitting transducer as measured along the direction of radiation of the sonic energy. This configuration of each set of transducers is superior to that of some other arrangement, such as a side-by-side arrangement, in that reflection can be obtained over a wider range of azimuthal angles from more widely dispersed sources of reflection such as flaws in the metal of the vessel wall. In view of this increased azimuthal coverage, it has now become advantageous, as taught by the invention, to combine four of the sets of transducers in a single array which can have a generally square shape of circular shape depending on the radius of curvature of the radiating surfaces. Thereby, greater speed and precision of measurement can be obtained for a more efficient locating of subsurface flaws in a vessel wall.

It is to be understood that the above described embodiment of the invention is illustrative only, and that modifications thereof may occur to those skilled in the art. Accordingly, this invention is not to be limited to the embodiment disclosed herein, but is to be limited only as defined by the appended claims.

I claim:

1. A transducer system for detection of flaws in the wall of a vessel carrying a liquid comprising:
    plural sets of transducers which make a conversion between electric energy and sonic energy;
    sled means for transporting said transducers along a surface of said wall covered by said liquid, the radiating surfaces of said transducers being submerged in said liquid, there being a layer of liquid between said radiating surfaces and said wall;
    each of said sets including a transmitting transducer and a receiving transducer directed towards a common region of said wall, the transducer in each set being arranged in tandem;
    said sets of transducers being supported by said sled means in a symmetrical array about said region of said wall;
    electric circuit means coupled to said transducer for the generating and receiving of sonic energy signals for locating flaws in said wall; and wherein
    in each of said sets, said transmitting transducer is inclined relative to a normal to said surface for directing radiation within said wall in a direction transverse to said normal for detection of a flaw at a site distant from the location of said transmitting transducer, said transmitting and receiving transducers being disposed with parallel longitudinal axes located for receiving radiation reflected from said site along a direction generally parallel to an intersection of said surface with said plane, thereby to maximize a combined beamwidth of said transmitting transducer and said receiving transducer.

2. A system according to claim 1 wherein there are four sets of said transducers diametrically positioned about a sonic window in said sled means.

3. A system according to claim 2 wherein said sonic window is an opening in said sled.

4. A system according to claim 1 wherein the radiating surfaces of transducers of separate ones of said sets are adjacent each other and are curved to provide substantially a circular array of transducers.

5. A system according to claim 1 wherein said transducers are angled at approximately 60 degrees relative to said normal to the surface of said wall for propagating sonice energy within and along said wall to subsurface sites for location of points of reflection at such subsurface sites.

6. A system according to claim 1 wherein said circuit means includes means for sequentially transmitting signals from sequential ones of said transducer sets.

7. A transducer system for detection of flaws in the wall of a vessel carrying a liquid comprising:
    plural sets of transducers which make a conversion between electric energy and sonic energy;
    sled means for transporting said transducers along a surface of said wall covered by said liquid, said sled means including pads for elevating said sled above said surface for spacing apart the radiating surfaces of said transducers from said surface to permit a layer of liquid to lay between said radiating surfaces and the surface of said wall to provide a sonic path therebetween;
    each of said sets including a transmitting transducer and a receiving transducer directed towards a common region of said wall, the transducers in each set being arranged in tandem with the radiating aperture of the receiving transducer being positioned behind the radiating aperture of the transmitting transducer;

said sets of transducers being supported by said sled means in an array about said region of said wall;

electric circuit means coupled to said transducers for generating and receiving sonic energy signals for the location of flaws in said wall; and wherein in each of said sets, said transmitting transducer is inclined relative to a normal to said surface for directing radiation within said wall in a direction transverse to said normal for detection of a flaw at a site distant from the location of said transmitting transducer, said transmitting and receiving transducers being disposed with parallel longitudinal axes located in a plane containing said normal for receiving radiation reflected from said site along a direction generally parallel to an intersection of said surface with said plane, thereby to maximize a combined beamwidth of said transmitting transducer and said receiving transducer.

8. A system according to claim 7 wherein each of said pads incorporates rollers said sled to roll along the surface of said wall at a predetermined height above said surface of said wall.

9. A system according to claim 8 wherein said sled means includes a sonic window, said transducers being positioned about said sonice window and angled at approximately 60 degrees relative to said normal to said wall surface for direction of sonic energy into said wall for propagation along and within said wall to subsurface sites of reflectance, and wherein said electric circuit means provides for the generation of a pulse of sonic energy having a duration less than the round-trip propagation time of a sonic energy pulse to a flaw in said wall.

10. A system according to claim 9 wherein said transducers are symmetrically positioned about said sonic window, there being four of said receiving transducers evenly spaced around said sonic window and having radiating apertures adjacent each other to provide a substantially square-shaped array.

* * * * *